United States Patent [19]

Uhlig

[11] Patent Number: 5,173,216

[45] Date of Patent: Dec. 22, 1992

[54] COMPOSITION FOR DECONTAMINATING AND/OR DISINFECTING THE HANDS, DISPENSABLE BY SOAP DESPENSERS

[75] Inventor: Bernd G. Uhlig, Frankfurt am Main, Fed. Rep. of Germany

[73] Assignee: CWF-Chemie Frankfurt GmbH, Maintal-Dornigheim, Fed. Rep. of Germany

[21] Appl. No.: 768,392

[22] PCT Filed: Mar. 21, 1990

[86] PCT No.: PCT/EP90/00463

§ 371 Date: Sep. 18, 1991

§ 102(e) Date: Sep. 18, 1991

[87] PCT Pub. No.: WO90/11342

PCT Pub. Date: Oct. 4, 1990

[30] Foreign Application Priority Data

Mar. 25, 1989 [DE] Fed. Rep. of Germany ..... 89105348

[51] Int. Cl.$^5$ .......................... C11D 1/62; C11D 1/65
[52] U.S. Cl. .................................... 252/547; 252/544; 252/550; 252/558; 252/DIG. 5; 514/563
[58] Field of Search ................ 252/8.6, 8.8, 544, 547, 252/548, 550, 558, DIG. 5; 514/563; 562/561, 564

[56] References Cited

U.S. PATENT DOCUMENTS

| 4,020,155 | 4/1977 | Kalopissis et al. | 562/564 |
| 4,124,632 | 11/1978 | Kalopissis et al. | 562/561 |
| 4,203,872 | 5/1980 | Flanagan | 252/547 |

FOREIGN PATENT DOCUMENTS 1617701  5/1971  Fed. Rep. of Germany .
25458    2/1980  Japan .

Primary Examiner—A. Lionel Clingman
Assistant Examiner—M. Kopec
Attorney, Agent, or Firm—Perman & Green

[57] ABSTRACT

A composition for decontaminating and/or disinfecting the hands comprising an amphoteric-cationic surfactant, a cationic surfactant, a wetting agent which is compatible with the cationic surfactant, and a nonionogenic regreasing agent is disclosed.

5 Claims, No Drawings

COMPOSITION FOR DECONTAMINATING AND/OR DISINFECTING THE HANDS, DISPENSABLE BY SOAP DESPENSERS

The invention relates to a preparation for decontaminating and/or disinfecting the hands, dispensable by soap dispensers.

Known means for hygienic and/or surgical disinfection of the hands are described in List VI of the Deutsche Gesellschaft fur Hygiene und Mikrobiologie [German Hygiene and Microbiology Society] (Hyg.+Med. 7 (1982) 467 ff).

The test of decontamination of the hands, provided for inclusion in the list, was amended in 1986 by the DGHM.

This applied in particular to the exposure time during which the germ count is to be reduced 3-log stages (=99.97%). It was reduced to 30 seconds because the former regulation specifying 2 minutes was not practical and required modification of behavior learned since childhood for cleaning the hands.

The shortened exposure time however meant that only certain active disinfecting agents met the requirements. These include low-molecular-weight alcohols (ethanol, n-propanol, isopropanol) as well as iodine, usually bound in complexes for stabilization.

Amphoterics and cationic surfactants are also used, but in combination with alcohols or iodophors.

The substances have a number of serious disadvantages, especially the following
they sharply attack the skin because the alcohols are highly degreasing or detergent and there is no possibility of replacing the grease or oils at the same time as disinfection;
their use in soap dispensers and hence elimination of further problems caused by germs is impossible in practice as a consequence of their aggressiveness or solvent power. This is especially true for plastic soap dispensers since attack by iodophors and/or alcohols very quickly renders the mechanical parts of the containers unusable due to migration and swelling of the plastic;
usability of this soap solution, which is in gel form as a rule, does not permit further modification to dispense it in a foam form, which requires only minimal water, and hence limits the introduction of germs from the tap water, since soaps which contain alcohol act to destroy the foam.

From this incomplete listing of the disadvantages of the prior art recited at the outset, there results the statement of the goal, namely to develop a preparation which, with the same disinfecting and decontaminating action, is not aggressive or harsh to the skin and imposes practically no limitation on the choice of materials for the soap dispenser.

The goal of the invention is to provide a substance for decontamination and/or disinfection of the hands whose combination is staggered so that it meets the requirements for disinfection of the hands which causes a reduction of the germs in 3-log stages, i.e. by 99.7%, assuming a wetting power roughly equivalent to that of alcohols This goal is acheived by a substance in accordance with the main claim.

Maximum skin protection is provided by avoiding highly degreasing alcohols in conjunction with the use of regreasing agents.

The substance can be dispensed by normal soap dispensers because the frequently observed attack of plastics by iodophors and/or alcohols, i.e. by migration or swelling, is avoided.

Similarly, destruction of composition prepared as foams is ruled out since the destructive alcohols are eliminated or excluded.

The composition claimed according to the invention is advantageously composed as follows:
a) 1 to 8 parts by weight of an amphoteric-cationic surfactant with the following structure:
N[N'(N''-alkyl-N''-carboxyalkyl) aminoethylcarbamoylmethyl]-N,N-dimethyl-N-alkylammonium chloride:

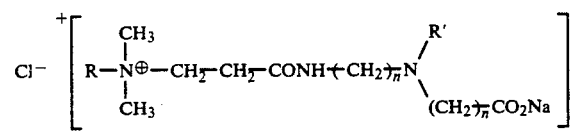

where
R = $C_{12}$–$C_{18}$ alkyl
R' = $C_1$–$C_4$ alkyl or $C_1$ to $C_4$ hydroxyalkyl and n = 1–4;
b) 2 to 10 parts by weight of another cationic surfactant of the benzalkonium chloride type;
c) 0.5 to 3 parts by weight of a wetting agent compatible with cationic surfactants, such as sulfosuccinates (diisooctyl sulfosuccinate), naphthtaline sulfonate (sodium diisooctylnaphthalenesulfonate) or amine oxides (lauryldimethylamine oxide);
d) 1 to 4 parts by weight of a nonionic regreasing agent like those known from cosmetic preparations (such as for example fatty acid alkanolamides or ethoxylated partial glycerides).

The substance which can be placed in a foam soap dispenser contains
4 wt.% N-[N''-(N''-hydroxymethyl-N''-carboxymethyl)aminoethylcarbamoylmethyl]-N,N-dimethyl-N-(coconut oil) ammonium chloride
4 wt.% lauryl dimethylammonium methosulfate
1 wt.% diisooctyl sulfosuccinate
2 wt % lauric acid monoethanolamide.

In the foam soap dispenser this mixture produces a light, creamy, fine-bubbled foam that leaves the skin feeling soapy smooth after the hands are rubbed together.

The following example is given of a preparation for disinfecting the hands:
3 parts N-[N,(N''-hydroxyethyl-N''-carboxyethyl) aminoethylcarbamoylmethyl]-N,N-dimethyl-N-laury-lammonium chloride,
5 parts benzalkonium chloride,
1 part lauryldimethylamine oxide
2 parts coconut oil acid monoethanolamide
89 parts water
100 parts liquid soap Following a test by a reputable institution, whose objective statement is included in full below, the following results were obtained:
As requested, we have tested to determine whether the liquid soap has any germ-killing properties against bacteria, yeasts, and molds. Testing consisted of a load test.

Test germs: *Escherichia coli* ATCC 15442, *Staphylococcus aureus* ATCC 6538 *Bacillus subtilis* ATCC 6051

*Candida abicans* ATCC 10231 *Asperoillus niger* ATCC 9642.

Findings: There are clearly evident antimicrobial properties against all test germs.

For a closer study of these antimicrobial properties, tests were conducted in accordance with the DGHM guidelines for testing and evaluation of chemical disinfecting methods.

1. Dilution Test

Test germs: *Escherichia coli, Pseudomonas aeruginosa, Staphylococcus aureus. Proteus mirabilis, Candida albicans.*

Findings: Bacteriostatic and fungistatic effectiveness still exists at a concentration of about 25%. Since the preparation is used undiluted, reliable effectiveness exists.

2. Suspension Tests a) Qualitative

Test germs same as dilution test Using approximately $10^8$ germs/ml, a test was conducted to determine how long it took to kill the test germs.
Results

| Test germs: | *Escherichia coli* | *Pseudomonas aeruginosa* | *Staph. aureus* |
|---|---|---|---|
| Time: | 1.0 min. | 2.0 min. | 0.5 min. |
| Test germs: | *Proteus mirabilis* | *Candida albicans* | |
| Time: | 2.0 min. | 1.0 min. | | b) Quantative

Test germs: *Staphylococcus aureus, Proteus mirabilis*

Using approximately $10^8$ germs/ml, a test was conducted to determine death rates as a function of exposure time in the presence of protein (0.2 bovine albumin) and in the absence of protein.
Results:

| Test germs: | *Staph. aureus* | |
|---|---|---|
| | with protein | without protein |
| Exposure time: | 0.5/1/2/5 | 0.5/1/2/5 min. |
| Death rate in %: | 100----- | 100--- |
| Test germs: | *Proteus mirabilis* | |
| | with protein | without protein |
| Exposure time: | 0.5/1/2/5 | 0.5/1/2/5 min. |
| Death rate in %: | 99.6, 99.9, 100- | 99.7, 99.9, 100- |

Evaluation: The product tested possesses good antimicrobial properties and is basically suitable for decontaminating the hands. There is no significant protein error.

Test No. 8805ML30531+8807ML37577 "

I claim:

1. Composition for decontaminating and/or disinfecting the hands, and being dispensable from soap dispensers, characterized in that it contains a combination of
   a) 1 to 8 parts by weight of an amphoteric-cationic surfactant with the structure:

N[N'(N''-alkyl-N''-carboxyalkyl aminoethylcarbamoylmethyl]-N,N-dimethyl-N-alkylammonium chloride

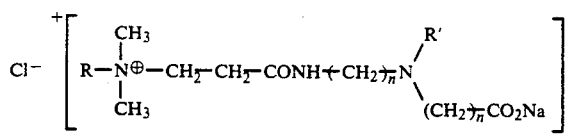

where
$R = C_{12}-C_{18}$ alkyl
$R' = C_1-C_4$ alkyl of $C_1$ to $C_4$ hydroxyalkyl and $n = 1-4$, b) 2 to 10 parts by weight of a cationic surfactant selected from the group consisting of benzalkonium chloride and lauryl dimethylammonium methosulfate,
   (c) 0.5 to 3 parts by weight of a wetting agent compatible with cationic surfactants, selected from the group consisting of sulfosuccinates naphthalene sulfonate and amine oxides, and
   d) 1 to 4 parts by weight of a nonionogenic regreasing agent.

2. Composition for decontaminating and/or disinfecting the hands according to claim 1, characterized in that it contains;
   a) 1 to 8 parts by weight N-[N'(N''-hydroxymethyl-N''-carboxymethyl) aminoethylcarbamoylmethyl]-N,N-dimethyl-N-(coconut oil) ammonium chloride,
   b) 2 to 10 parts by weight lauryl dimethylammonium methosulfate,
   c) 0.5 to 3 parts by weight diisooctyl sulfosuccinate, and
   d) 1 to 4 parts by weight lauric acid monoethanolamide.

3. Composition according to claim 1 in which the wetting agent component (c) is selected from the group consisting of diisooctyl sulfosuccinate, sodium diisooctyl naphthalenesulfonate and lauryl dimethylamine oxide.

4. Composition according to claim 1 in which the regreasing agent component (d) is selected form the group consisting of fatty acid alkanolamide sand ethoxylated partial glycerides.

5. Composition for decontaminating and/or disinfecting the hands according to claim 1, characterized in that it contains:
   A) 1 to 8 parts by weight N-[N'(N''-hydroxyethyl-N''-carboxyethyl)aminoethylcarbamoylmethyl]-N,N-dimethyl-N-laurylammonium chloride,
   B) 2 to 10 parts by weight benzalkonium chloride,
   C) 0.5 to 3 parts by weight lauryldimethylamine oxide,
   D) 1 to 4 parts by weight coconut oil acid monoethanolamide.

* * * * *